United States Patent [19]

Resnik

[11] Patent Number: 5,788,660
[45] Date of Patent: Aug. 4, 1998

[54] ANCHOR FOR SURGICAL DRESSING

[76] Inventor: Julie M. Resnik, 3 Willi La., Ellington, Conn. 06029

[21] Appl. No.: 953,060

[22] Filed: Oct. 20, 1997

[51] Int. Cl.⁶ ............................................. A61F 13/00
[52] U.S. Cl. ........................... 602/79; 606/215; 602/41
[58] Field of Search ........................... 606/213, 216; 602/79, 41

[56] References Cited

U.S. PATENT DOCUMENTS

| | | | |
|---|---|---|---|
| 3,417,749 | 12/1968 | Bailey | 602/79 |
| 3,724,457 | 4/1973 | Klatte | 602/79 |
| 3,779,242 | 12/1973 | McCullough | 602/79 |
| 3,968,803 | 7/1976 | Hyman | 602/79 |
| 4,732,146 | 3/1988 | Fasline et al. | 602/79 |
| 5,456,660 | 10/1995 | Reich et al. | 602/79 |
| 5,538,502 | 7/1996 | Johnstone | 602/79 |
| 5,593,963 | 1/1997 | Hall | 602/75 |
| 5,665,108 | 9/1997 | Galindo | 606/215 |

*Primary Examiner*—Richard J. Apley
*Assistant Examiner*—Kim M. Lee
*Attorney, Agent, or Firm*—M. P. Williams

[57] ABSTRACT

An anchor 9 for a surgical dressing includes a sheet 12 with eyelets 13 therein, said sheet attached to a layer of elastic and flexible polymeric foam 20 having an adhesive layer 30, such as a hydrocolloid or polyisobutylene adhesive. The foam is at least 10 mils thick and preferably in the range of 70 mils to 90 mils thick. The eyelets may have reinforcements 18, 24.

17 Claims, 1 Drawing Sheet

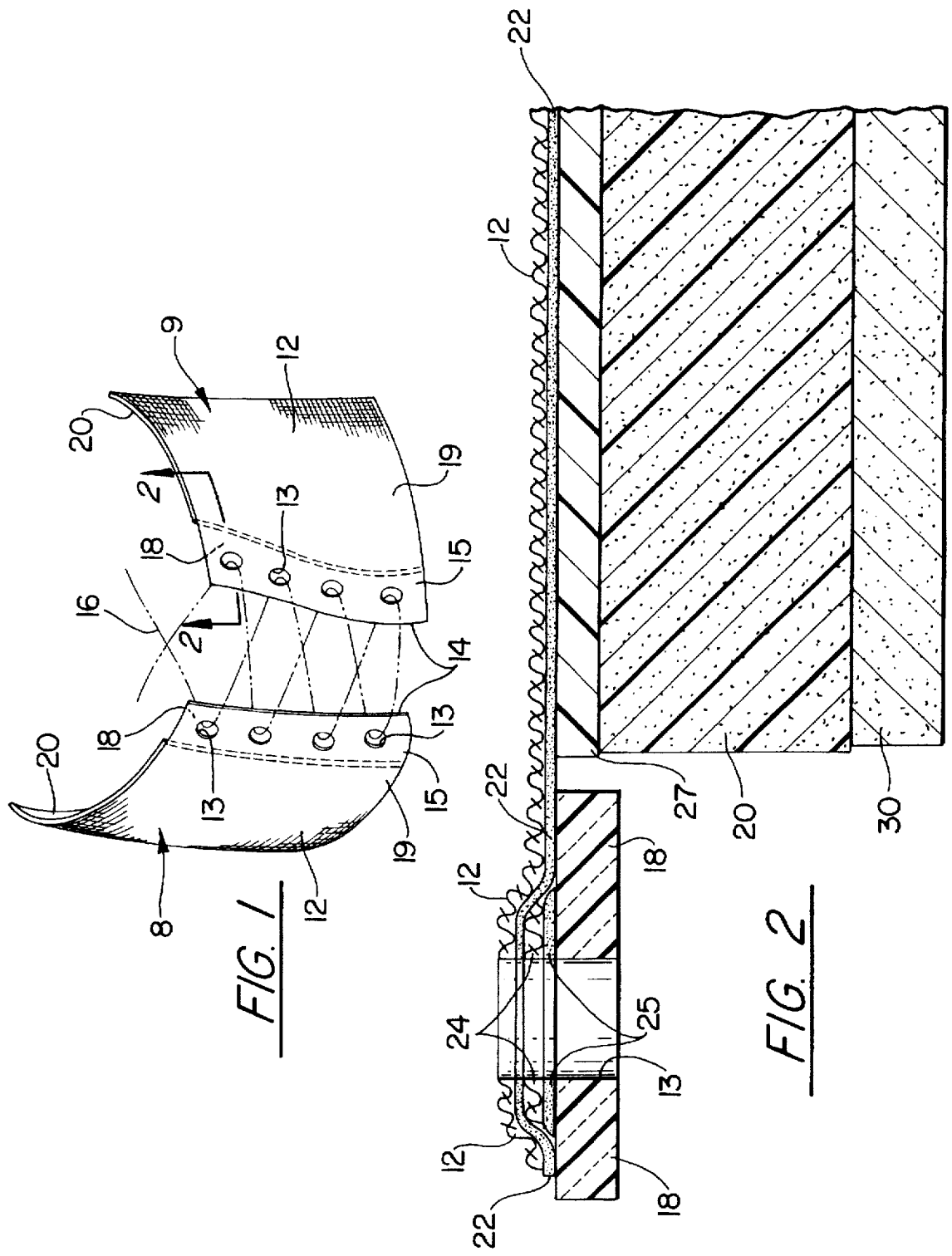

5,788,660

1
ANCHOR FOR SURGICAL DRESSING

TECHNICAL FIELD

This invention relates to an anchor for surgical dressings which is secured to the body of a patient by means of a polymeric foam pad utilizing a moisture-tolerant, patient-friendly adhesive, such as a hydrocolloid or polyisobutylene adhesive.

BACKGROUND ART

The application of dressings to large open wounds, second degree burns and skin donor sites has evolved from harnesses which, when in place securing a bandage, would surround an entire body part, to today's semi-open cell polymeric flexible foam pads having hydrocolloid or polyisobutylene wettable adhesives. The modern pads are very useful when the wound need not be attended for several days at a time, however, some wounds need to be cleaned and dressed daily, or even more frequently. For this type of wound, a surgical dressing is typically secured by a pair of anchors which are held in place on the skin of the patient by means of adhesive, and which has eyelets therein to permit securing with cord (lacing) or in some other fashion, such as with rubber bands held to the eyelets with safety pins. Such anchors have typically been referred to as "Montgomery straps". One current brand of Montgomery strap consists of thin silk cloth with an adhesive extending across the entire surface of one side thereof. An extra layer of silk is provided in the region of the strap where eyelets are formed, and a layer of 10 mil (or thereabouts) vinyl extends from the edge near the eyelets inwardly past the eyelets, so as to shield the dressing and the body of the patient from the adhesive in the region near the eyelets. The remainder of the adhesive becomes exposed when a peel-layer is removed, in use. However, this type of Montgomery strap does not allow the skin to breath, causing skin breakdown, skin tears and rashes, which prevents repetitive use in the same area. It has been found to be very irritable to patients, and resulting in significant discomfort from its use. It does not conform well to body topography which is highly dimensional, it has a tendency to creep, and it does not adhere well.

DISCLOSURE OF INVENTION

This invention is predicated on the discovery that the problem with present day Montgomery straps is actually three-fold. First, the adhesive must be of a type generally similar to those used for polymeric foam wound dressings (referred to hereinbefore) or ostomies; that is, it should be breathable, moisture-tolerant and patient-friendly (such as substantially hypoallergenic); second, the material which is adhered to the skin need not only be flexible, but elastic in all dimensions so that it can stretch at least a little bit where needed to conform to body parts, and return to its original size as appropriate; and, third, there needs to be flexibility between the structure which holds the eyelets and the material which is adhered to the skin of the patient, so that the eyelet structure does not unyieldingly pull on the skin.

According to the present invention, an anchor for surgical dressings comprises a sheet of material having an eyelet, for receiving a tying device, a layer of elastic and flexible polymeric foam attached to the sheet, with a breathable, moisture-tolerant, patient-friendly adhesive disposed on a side of said foam opposite to said sheet, for adhering to the skin of a patient.

Other objects, features and advantages of the present invention will become more apparent in the light of the following detailed description of exemplary embodiments thereof, as illustrated in the accompanying drawing.

BRIEF DESCRIPTION OF THE DRAWINGS

FIG. 1 is a perspective view of a pair of anchors for surgical dressings in accordance with the invention.

FIG. 2 is a bottom cross sectional view taken on the line 2–2 of FIG. 1 with the thickness of the various layers greatly exaggerated and not to any common scale.

BEST MODE FOR CARRYING OUT THE INVENTION

Referring now to FIG. 1, a pair of anchors 8, 9 for surgical dressings, when used together as shown in FIG. 1, will adhere to the body of a patient and secure a surgical dressing thereto. Each anchor 8, 9 comprises a web sheet 12 or having at least one eyelet 13 formed near a first edge 14 of a first portion 15 thereof. The two anchors 8, 9 may be secured together over a dressing by lacing 16 (shown in phantom in FIG. 1) or by means of rubber bands secured to the eyelets 13 by safety pins, or in any other suitable fashion. The first portion 15 of each of the anchors 8, 9 may have vinyl sheeting 18 secured thereto, as reinforcing for the eyelets 13. A second portion 19 of each of the anchors 8, 9 has an elastic and flexible polymeric foam pad 20 disposed thereon.

Referring now to FIG. 2, the sheet 12 may have a layer of adhesive 22 covering substantially the entire patient-side of the sheet 12. In FIG. 2, the sheet 12 is configured as woven cloth, and it may preferably comprise silk, of a type commonly used in Montgomery straps. An additional piece of silk 24 may be used throughout the first portion 15 (FIG. 1) or only in the vicinity of the eyelets 13 so as to provide reinforcement for the eyelets. If additional silk 24 or other material is used for eyelet reinforcement, it will have a layer of adhesive 25 disposed thereon so as to assist in bonding the vinyl lamination 18 to the sheet 12. If the foam 20 is formed separately from the remainder of the anchor 9 and later joined thereto, it may preferably have an elastic, polymeric film 27, having a thickness on the order of 2 mils, adherent to substantially the entire surface of the side of the foam 20 which is adhered to the sheet 12. The film 27 principally strengthens the foam in the case where the foam is semi-open cell foam. On the other hand, if the foam 20 is closed cell or if it is formed and joined directly to the sheet 12, the film 27 may not be necessary.

An adhesive layer 30 is adherent to substantially the entire surface of the patient-side of the foam 20. In accordance with one aspect of the invention, the adhesive 30 comprises a moisture-tolerant, patient-friendly adhesive, which is wettable but maintains its adherence without irritation or injury to the skin of the patient. As examples, the adhesive may be a hydrocolloid adhesive, a number of which are disclosed in U.S. Pat. No. 4,231,369. Or, the adhesive may be a polyisobutylene adhesive, such as those described in U.S. Pat. Nos. 4,393,150 and 4,147,831. Or the adhesive may be a combination polyisobutylene/hydrocolloid adhesive such as those described in U.S. Pat. Nos. 3,972,328; 4,147,831; 4,166,051; 4,231,369; 4,253,460, 4,393,080; and 4,551,490.

The foam 20, with or without the film 27, may be of the type described in U.S. Pat. No. 3,972,328. Alternatively, the foam, with or without the film 27 and adhesive 30 may take the form of those commercially available under the trade names ExuDERM (a trademark of Medline Industries, Inc.) and DuoDERM (a trademark of ConvaTec, a Bristol-Myers Squibb Company). The sheet 12 and adhesive 22, with or without the additional material 24, adhesive 25 and vinyl lamination 18, may take the form of a commercially available Montgomery strap from Johnson & Johnson. The foam 20 should be at least 10 mils thick to provide mechanical resilience between the sheet 12 and the adhesive 30. A preferred range of thickness is between 70 mils and 90 mils, but foam between 50 mils and 120 mils is also useful. All the foregoing variations are not relevant to the invention, it suffice that the material which supports the eyelets be joined to the skin through a sufficiently thick elastic, flexible foam pad to permit contouring to the patient and absorbing strain impressed thereon by the eyelets, by means of a patient-friendly resilient adhesive which has reliable adherence to skin. All of the aforementioned patents are incorporated herein by reference.

Thus, although the invention has been shown and described with respect to exemplary embodiments thereof, it should be understood by those skilled in the art that the foregoing and various other changes, omissions and additions may be made therein and thereto, without departing from the spirit and scope of the invention.

I claim:

1. An anchor for a surgical dressing, comprising:
   a sheet having a first edge and a second edge opposite to said first edge, a first portion of said sheet extending inwardly from said first edge, and a second portion of said sheet extending inwardly from second edge to said first portion;
   an eyelet, for receiving a tying device, formed in said first portion near said first edge; and
   an adhesive layer substantially coextensive with said second portion;
   wherein the improvement comprises:
      a layer of elastic and flexible polymeric foam having one side attached between a surface of said second portion and said adhesive layer, said layer being at least 10 mils thick; and
      said adhesive layer comprising a breathable, moisture-tolerant, patient-friendly adhesive disposed on a side of said foam opposite said one side.

2. An anchor according to claim 1 wherein said adhesive layer comprises a hydrocolloid or polyisobutylene adhesive.

3. An anchor according to claim 1 comprising a plurality of eyelets disposed along said first edge.

4. An anchor according to claim 1 wherein said eyelet is reinforced.

5. An anchor according to claim 4 wherein said eyelet is reinforced with a layer of sheeting adherent to said sheet.

6. An anchor according to claim 5 wherein said layer of sheeting is the same material as the material of said sheet.

7. An anchor according to claim 1 wherein said eyelet is reinforced by a flexible vinyl lamination adherent to said surface.

8. An anchor according to claim 1 wherein said sheet is a web.

9. An anchor according to claim 1 wherein said sheet is woven silk.

10. An anchor according to claim 1 including an adhesive lamina between said foam and said surface.

11. An anchor according to claim 1 wherein said layer of flexible polymeric foam is attached to said surface by an elastic polymeric film adherent to said foam and an adhesive lamina between said film and said surface.

12. An anchor according to claim 1 wherein said foam is selected from polyester or polyether polyurethane foams, and styrene-butadiene foams.

13. An anchor according to claim 12 wherein said foam is semi-open cell polyurethane foam.

14. An anchor according to claim 1 wherein said layer is between 40 mils and 120 mils thick.

15. An anchor according to claim 1 wherein said layer is between 70 mils and 90 mils thick.

16. An anchor for a surgical dressing, comprising:
   a sheet having a first edge and a second edge opposite to said first edge, a first portion of said sheet extending inwardly from said first edge, and a second portion of said sheet extending inwardly from said second edge to said first portion;
   an eyelet, for receiving a tying device, formed in said first portion near said first edge; and
   an adhesive layer substantially coextensive with said second portion;
   wherein the improvement comprises:
      a layer of elastic and flexible polymeric foam having one side attached between a surface of said second portion and said adhesive layer, said layer being at least 10 mils thick; and
      said adhesive layer comprising a hydrocolloid or polyisobutylene adhesive disposed on a side of said foam opposite said one side.

17. An anchor for a surgical dressing, comprising:
   a sheet having a first edge and a second edge opposite to said first edge, a first portion of said sheet extending inwardly from said first edge, and a second portion of said sheet extending inwardly from said second edge to said first portion;
   an eyelet, for receiving a tying device, formed in said first portion near said first edge; and
   an adhesive layer substantially coextensive with said second portion;
   wherein the improvement comprises:
      a layer of elastic and flexible polymeric foam having one side attached between a surface of said second portion and said adhesive layer, said layer being at least 10 mils thick; and
      said adhesive layer comprising a hydrocolloid adhesive disposed on a side of said foam opposite said one side.

* * * * *